United States Patent [19]

Davidson et al.

[11] Patent Number: 5,107,852

[45] Date of Patent: Apr. 28, 1992

[54] CATHETER GUIDEWIRE DEVICE HAVING A COVERING OF FLUOROPOLYMER TAPE

[75] Inventors: Daniel F. Davidson; Larry J. Kovach, both of Flagstaff; David J. Myers, Camp Verde, all of Ariz.

[73] Assignee: W. L. Gore & Associates, Inc., Newark, Del.

[21] Appl. No.: 503,189

[22] Filed: Apr. 2, 1990

[51] Int. Cl.⁵ .................................................. A61B 5/02
[52] U.S. Cl. ..................................... 128/772; 604/164; 604/282; 604/265
[58] Field of Search .................. 29/173; 156/143, 144, 156/187, 195, 86; 128/772, 207.14, 207.15

[56] References Cited

U.S. PATENT DOCUMENTS

| | | |
|---|---|---|
| 3,223,564 | 12/1965 | Buschman et al. . |
| 3,711,917 | 1/1973 | Baumgras . |
| 3,757,768 | 9/1973 | Kline . |
| 3,841,308 | 10/1974 | Tate . |
| 3,922,378 | 11/1975 | Kline ................................... 128/772 |
| 3,973,556 | 8/1976 | Fleischhacker et al. . |
| 4,003,369 | 1/1977 | Heilman et al. . |
| 4,080,706 | 3/1978 | Heilman et al. . |
| 4,456,017 | 6/1984 | Miles . |
| 4,479,835 | 10/1984 | Kutnyak et al. ..................... 156/143 |
| 4,534,363 | 8/1985 | Gold ..................................... 128/772 |
| 4,676,249 | 6/1987 | Arenas et al. ........................ 128/772 |
| 4,721,117 | 1/1988 | Mar et al. ............................. 604/282 |
| 4,779,528 | 10/1988 | Machek ................................ 128/772 |
| 4,817,630 | 4/1989 | Schintgen ............................ 128/772 |

Primary Examiner—Kyle L. Howell
Assistant Examiner—Scott R. Akers
Attorney, Agent, or Firm—Wayne D. House

[57] ABSTRACT

A catheter guidewire having a covering of a fluoropolymer tape. The tape may be applied either helically or longitudinally to the outer surface of the guidewire or to the surface of the wire from which the guidewire is made. Such a covering is inert, lubricious, flexible, will not flake, and can be applied as an extremely thin coating. Additionally, such a covering allows the guidewire to tolerate the application of greater force before uncoiling and wire breakage occurs.

Other catheter guidewire devices having fluoropolymer tape coverings are also described.

13 Claims, 10 Drawing Sheets

CATHETER GUIDEWIRE DEVICE HAVING A COVERING OF FLUOROPOLYMER TAPE

FIELD OF THE INVENTION

This invention relates to the field of catheter guidewires and catheter guidewire devices.

BACKGROUND OF THE INVENTION

Guidewires are used for directing catheters to precise locations within passageways of living bodies. These passageways are often of small inside diameter (as small as 0.020 inch), incorporate many branches and present tortuous, curved paths. The ideal guidewire must be break-resistant, flexible, kink-resistant, have a smooth and lubricious surface, have a minimal outside diameter, provide good torque characteristics and offer good column strength to allow the guidewire to be pushed through complex passageways like the vascular system.

A guidewire is typically inserted into a guiding catheter which was previously placed into the vascular system through a cannula device and pushed through the vascular system to the desired location by routing through the appropriate branches. Careful manipulation of the guidewire past the distal end of the guiding catheter is required while viewing the passage of the guidewire radiographically. After the distal tip of the guidewire is in the desired position, a catheter is inserted over the guidewire and moved along the length of the guidewire to the desired position.

Guidewires typically take the form of a tightly wound spring which is constructed of very fine wire tightly wrapped into a helically wound coil spring in which adjacent turns typically contact each other. Guidewires are generally available as small as 0.014 inch outside diameter formed from round-section wire of diameter as small as 0.002 inches. Wires of essentially square and rectangular cross-section have been used as well, as have round wires with their outer surface ground flat in order that the guidewire may present a flat surface to the tissue walls.

In use, breakage of the helically wound guidewire is known to occur on occasion, resulting in the separation and loss of the distal end of the guidewire. Surgical intervention is often required to retrieve the lost end. It is common practice to employ a safety wire oriented along the axis of the guidewire to prevent the loss of a broken distal guidewire portion. This is accomplished by suitably attaching (welding, brazing, etc.) the tip of the safety wire to the tip of the guidewire. The use of safety wires has reduced the frequency of breakage and loss of the distal end, but has not eliminated it, apparently due to breakage of the safety wire or its attachment to the guidewire during the same trauma responsible for the breakage of the guidewire.

Some guidewires do not use a safety wire within the distal end portion of the device so that the device tip may be as flexible as possible. It is this distal end portion that is most commonly broken and lost.

Breakage of these devices generally appears to follow the same pattern. In attempting to pass the guidewire around a sharp bend or through an obstructed passageway, the tip of the device becomes trapped. The operator generally attempts to free the device with rotary, extension (compression) and traction (tensile) forces. The application of an excessive traction force results in uncoiling of the guidewire. If this traction force is then relieved momentarily, the uncoiled length of guidewire tries to recover at least some of its previously coiled form. The application of a rotary force to the partly uncoiled wire appears to result in tangling of the wire as the uncoiled wire loops or crosses over itself in one or more places. Continued application of rotary and/or traction forces causes kinking of the tangled wire, which quickly results in breakage of the wire at the location of a kink.

Uncoiling is herein meant to mean extension of the coil spring beyond its elastic limit.

Guidewires have been available for some time with plastic coatings, most frequently of polytetrafluoroethylene (hereinafter PTFE). This is done so as to present a smooth, lubricious and inert surface to the vessel wall. Such coatings have been applied to the outer surface of the guidewire coil and have also been applied to the circumferential surface of the wire before winding the wire into a coil so that the entire circumference of the wire surface is coated.

While previous PTFE coated guidewires have provided improved guidewire performance, these previous coatings still have significant shortcomings. PTFE coatings have typically been applied by either dip-coating the wire in a liquid dispersion of PTFE or by covering with PTFE heat-shrink tubing. Either method may be used to coat the circumferential surface of the wire before winding into a guidewire or to coat the outer surface of the already wound guidewire. Dip-coatings may be applied more thinly than heat-shrink tubing, however, such dip-coatings are prone to flaking during manipulation of the guidewire. Such flaking presents an undesirable risk of contamination to the patient. Heat-shrink coatings generally are not vulnerable to flaking, however, the use of such coatings results in a guidewire of increased outside diameter due to the increased thickness of the heat-shrink coating. Additionally, heat shrink tubing covering the distal end of small diameter guidewires significantly restricts flexibility.

SUMMARY OF THE INVENTION

A catheter guidewire is disclosed having a covering of a fluoropolymer tape. The tape can be applied either helically around the outer surface of the wound guidewire, or longitudinally around the outer surface of the wound guidewire, as in a cigarette wrap. Additionally, the tape can be applied around the circumferential surface of the wire comprising the guidewire before the wire is wound into the coiled form of the guidewire. It can also be applied around the circumferential surface of the axially oriented safety wire.

The use of a tape is advantageous for several reasons. A coating of fluoropolymer tape offers the same fundamental advantages of previous PTFE coatings, i.e., a lubricious and inert surface is presented to the living tissue. Additionally, the tape can be applied as an extremely thin covering, for example, about 0.0005 inches total thickness. Such a coating only minimally increases the outside diameter of the guidewire. The thin tape covering is not subject to flaking problems as are previous guidewire coatings applied in liquid form. It therefore offers the integrity of heat-shrink coverings in a previously unavailable extremely thin form. The tape covering also increases the ability of a guidewire tip to withstand rotary and traction forces without becoming uncoiled, thus reducing the likelihood of breakage.

Additionally, in cases where the circumferential surface of the wire is tape-wrapped prior to winding the wire into the form of a guidewire, the tape-wrapped covering on the wire makes it more difficult to break such a guidewire that has been uncoiled by excessive traction forces. While the uncoiled guidewire is still liable to tangling, it does not break so easily. This is apparently because the lubricious surface of the tape-wrapped wire prevents it from binding on itself during the tangling process, so that the subsequent application of rotary or traction forces does not produce a kink in the wire that quickly results in wire breakage.

The fluoropolymer tape coating can be a porous fluoropolymer. Porous tape coatings can be impregnated with other materials such as anticoagulants and lubricants and can be used to carry those other materials into body cavities.

Other types of catheter guidewire devices can also benefit from fluoropolymer tape-wrapping.

DETAILED DESCRIPTION OF THE INVENTION

This invention comprises a catheter guidewire having a tape-wrapped covering of a fluoropolymeric tape. Such a tape would preferably be either fluorinated ethylene propylene (hereinafter FEP) or PTFE. The PTFE tape may be of a porous form. A preferred material is expanded, porous PTFE having a microstructure of nodes interconnected by fibrils, manufactured as taught by U.S. Pat. No. 3,962,153, hereby incorporated by reference.

Other useful fluoropolymer materials include tapes cut from films of perfluoroalkoxy resin (PFA), polychlorotrifluoroethylene (PCTFE), ethylene-chlorotrifluoroethylene copolymer (ECTFE), ethylene-tetrafluoroethylene copolymer (ETFE), polyvinylidene fluoride (PVDF), and polyvinyl fluoride (PVF). "Tape" herein describes a thin and narrow strip of material of relatively long length, that when used as a covering material is capable of covering a useful length, for example, the length of a guidewire, preferably without the necessity of adding a second tape to augment the length of the first. Devices such as guidewires having a tape-wrapped covering may be identified by exposed edges of the covering tape material or by helical appearance of the covering tape material. Devices having coverings of dip-coated materials or of heat-shrink tubing materials will not have such exposed edges or helical appearances. Microscopy may be necessary to view these characteristics.

Tape-wrapped coverings may be applied to guidewires as extremely thin coverings. Fluoropolymer films are available of thinness approaching 0.0005 inch. These thin films may be cut into tapes to create the present invention. Tension applied to nonporous tape during the process of wrapping the guidewire can be such that the tape stretches during wrapping to provide a still thinner covering. The mechanical integrity of these fluoropolymer tapes is such that the finished guidewire covering, even in extremely thin form, is not subject to breaking up and flaking as are previous liquid-applied fluoropolymer thin coatings. While previous heat-shrink tubing coatings do not have the flaking problems of liquid-applied coatings, the heat-shrink coatings have not been previously available in extremely thin form. Thinness is desirable to minimize the outside diameter and maximize the flexibility of the finished guidewire.

Figure 1:
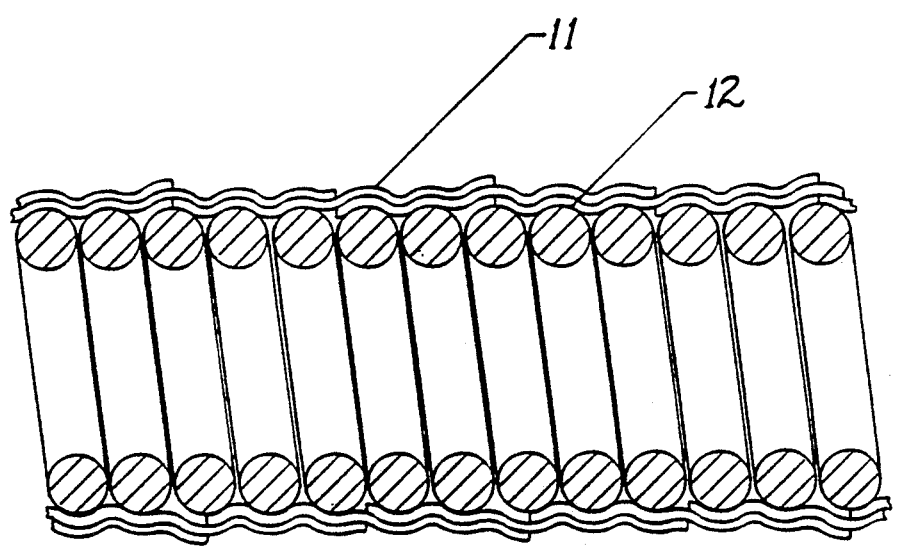
FIG. 1 shows a longitudinal section of a tape-wrapped guidewire wherein the tape has been helically wrapped around the outer surface of the previously wound guidewire.

As shown in FIG. 1, in one embodiment the tape 11 is wrapped helically around the outer surface of a previously wound guidewire 12. Such a helically-wound covering of fluoropolymer tape is practical regardless of the cross-sectional form of the wire comprising the guidewire.

Figure 2:
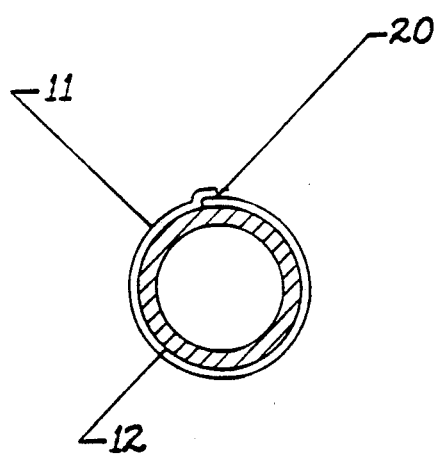
FIG. 2 shows a cross section of a tape-wrapped guidewire wherein the tape has been longitudinally wrapped around the outer surface of the previously wound guidewire in the fashion of a cigarette wrap, the edges of the tape being overlapped.
Figure 3:
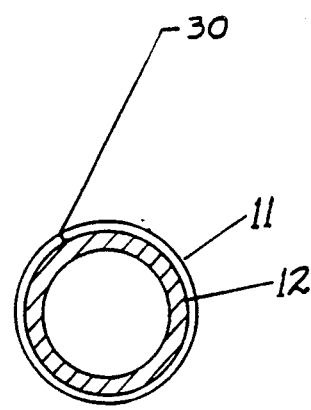
FIG. 3 shows a cross section of a tape-wrapped guidewire wherein the tape has been longitudinally wrapped around the previously wound guidewire in the fashion of a cigarette wrap, the edges of the tape being abutted.

The tape 11 may also be longitudinally applied to the outer surface 12 of a previously wound guidewire in the manner of a cigarette wrap so that the tape seam line is parallel to the guidewire axis. The seam may consist of either overlapped 20 or abutted 30 tape edges as shown respectively by the tape-wrapped guidewire cross-sections of FIGS. 2 and 3.

Figure 4:
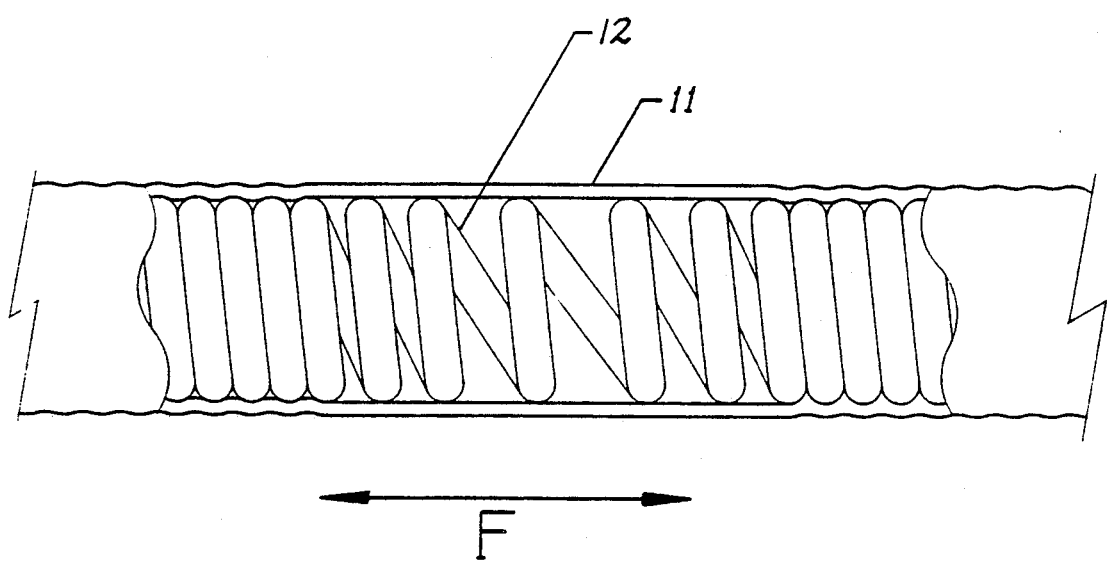
FIG. 4 shows a partially uncoiled guidewire wherein the tape is shown inhibiting further uncoiling of the guidewire.

Tape-wrapped guidewire outer surface coverings are capable of increasing the amount of force that the guidewire may withstand before uncoiling of the guidewire occurs. FIG. 4 shows how the tape-wrapped covering 11 absorbs some part of an uncoiling force F. As breakage of the guidewire may result from uncoiling, breakage can be forestalled by application of a tape-wrapped outer surface covering to a guidewire.

Figure 5:
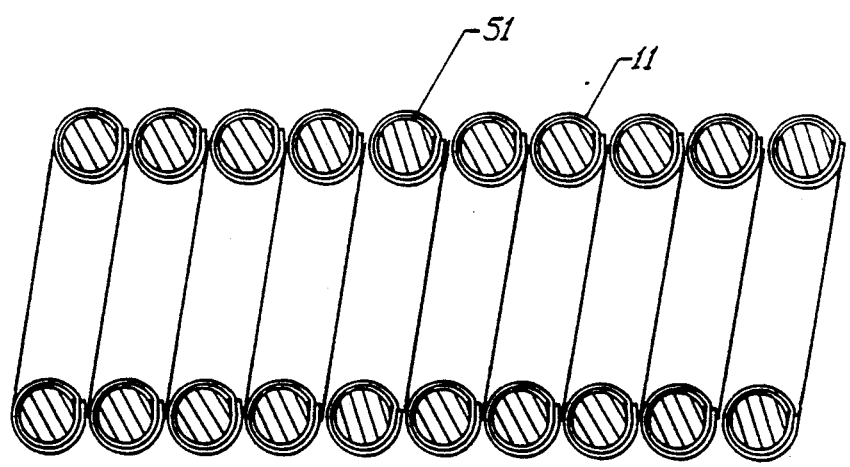
FIG. 5 shows a longitudinal section of a tape-wrapped guidewire wherein the tape has been wrapped around the circumferential surface of the wire comprising the guidewire before the guidewire is wound into the form of a coiled spring.

In a further embodiment of this invention, the tape may be applied to the circumferential surface of the wire comprising the guidewire before winding the wire into the coil-spring form of the guidewire. As shown by FIG. 5, the wire coils 51 of the guidewire are completely surrounded or encapsulated by the tape 11. The tape may be applied around the circumferential surface of the wire in either helical or cigarette wrap fashion.

Figure 6:
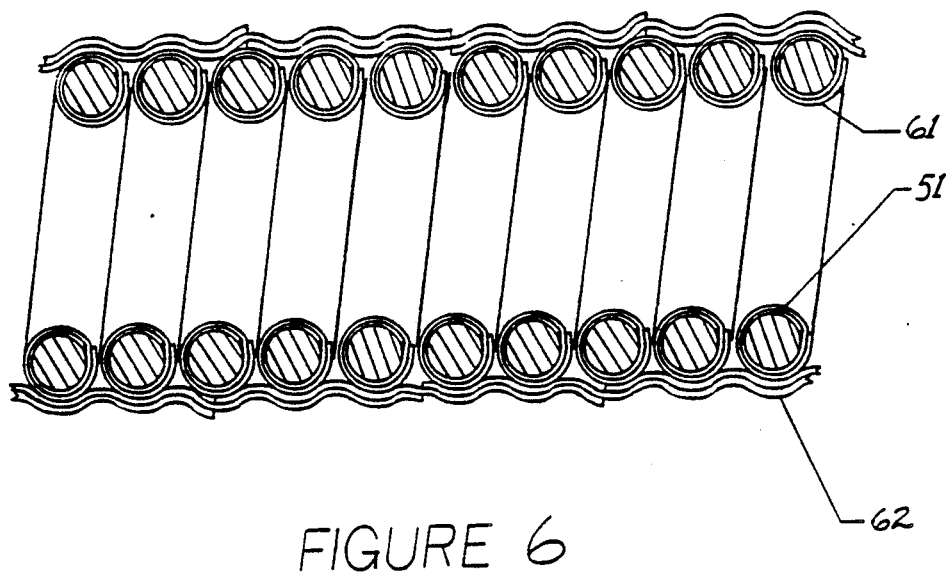
FIG. 6 shows a longitudinal section of a tape-wrapped guidewire wherein a first tape-wrapped covering has been applied to the circumferential surface of the wire before winding the wire into the form of a guidewire, and a second tape-wrapped covering has been applied to the guidewire outer surface after the wire has been wound into the form of a guidewire.

An additional embodiment of this invention is shown in FIG. 6 which shows a longitudinal section of a tape-wrapped guidewire wherein a first tape-wrapped covering 61 has been applied to the circumferential surface of the wire 51 before winding the wire into the form of a guidewire, and a second tape-wrapped covering 62 has been applied after the wire 51 has been wound into the form of a guidewire.

Figure 7:
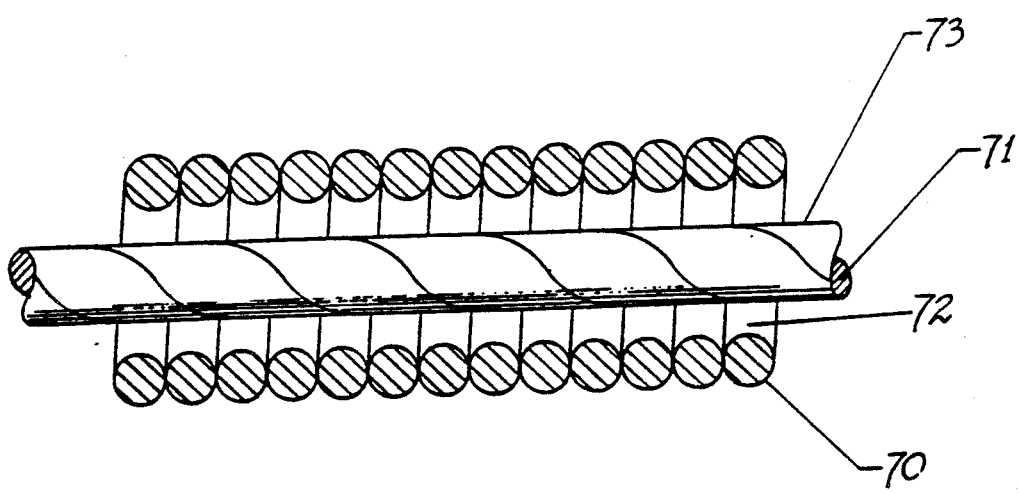
FIG. 7 shows a guidewire having an axially-oriented safety wire wherein the circumferential surface of the safety wire has been given a tape-wrapped covering.

As shown by FIG. 7, in a further embodiment of this invention, the axially-oriented safety wire 71 within the interior 72 of the guidewire 70 can also be provided with a thin and lubricious tape-wrapped fluoropolymer coating 73 without risk of flaking of the coating.

The following are some of the factors that may influence the handling characteristics of the tape-wrapped guidewire: the type of fluoropolymer and porosity (if any), the pitch of the helically wound wrap, the width and thickness of the tape used, the number of layers applied (taken at any cross section) and the direction of the wrap relative to the direction of the winding of the guidewire. In general, tapes may be applied in coverings so thin as to have little effect on the handling of the guidewire.

Preferred fluoropolymers for use as the tape material are FEP and PTFE. These materials are highly inert and can be expected to cause no adverse tissue reaction. They are highly lubricious, reducing the friction of the guidewire surface and easing its passage along vessel walls.

The most preferred fluoropolymer tape is porous PTFE. Such a material is porous, expanded PTFE having a microstructure of nodes interconnected by fibrils. The manufacture of this material is described in U.S. Pat. No. 3,962,153. That patent describes the manufacture of a porous, expanded PTFE film that, when slit into a narrow tape, is suitable for use as the tape-wrapped guidewire covering of this invention. The porous, expanded PTFE tape-wrapped covering is most preferred because in addition to being inert and lubricious, it has a greater tensile strength and flexibility than non-porous fluoropolymer tapes. This allows the use of even thinner tape coverings having adequate mechanical integrity to avoid damage and flaking during guidewire use.

The tape may be applied with equipment presently used for tape-wrapping applications such as, for example, insulating electrical wires and cables.

Figure 8:
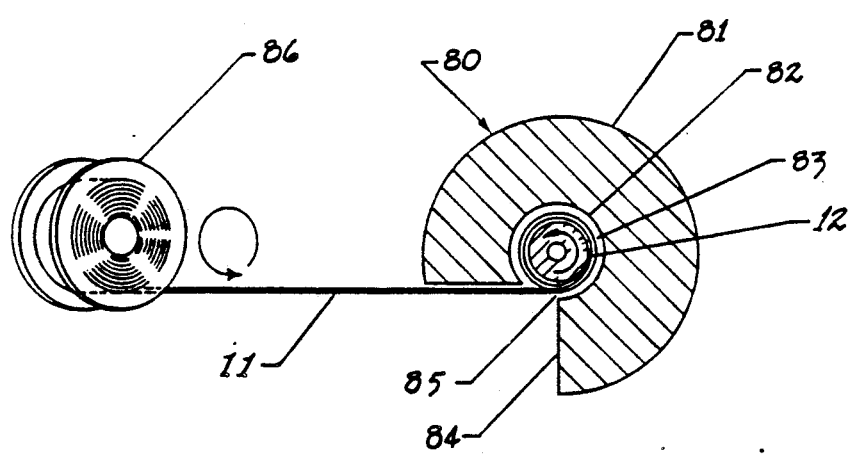
FIG. 8 shows a cross-section of a die that may be used in the application of tape to flexible guidewires.

FIG. 8 describes in cross section a die 80 that is useful in the application of tape to flexible guidewires where the flexibility of the guidewire causes difficulty in tape application. The die 80 consists of a cylinder 81, preferably of a lubricious plastic such as Delrin ® or PTFE, having a through-hole 82 along the axis of the cylinder, the through-hole being of diameter adequate to provide a slight clearance 83 beyond the diameter of the guidewire 12 after tape wrapping. The purpose of the through-hole is to serve as a guide to the rotating guidewire. The length of this cylinder should be adequate to support the guidewire in order to prevent any tendency to twist or kink during wrapping. The die has a section 84 cut away in order to provide an access slot 85 into the through-hole of the die. This slot 85 allows tape 11 to pay off of a spool 86 and feed onto the rotating guidewire 12 as the guidewire is simultaneously fed axially within the through-hole 82 of the die 80. The slot is preferably of the minimum width necessary to allow the tape to feed freely onto the rotating guidewire. A slot of minimum width offers the least possible interruption of the internal surface of the through-hole that serves to guide the rotating guidewire. FIG. 8 shows a ninety degree angular section 84 cut away to provide the access slot 85; the angle of the cut away section 84 is relatively unimportant.

After the application of the tape-wrapped covering to the guidewire, the assembly is preferably heated above the melt point of the fluoropolymer. This heat treating process thermally bonds adjacent surfaces of the tape together, i.e., bonds overlapping or abutting tape surfaces, thereby preventing the tape edges from coming loose and producing a bonded-together flexible covering.

In the case of wire that is tape-wrapped prior to winding into a guidewire, the heat treating process can be performed before the winding process to prevent bonding together the coated surfaces of adjacent windings. Alternatively, the heat treating process may be performed after the winding process if it is desired to bond together the coated surfaces of adjacent windings.

In the case of wire that has a first tape-wrapping applied to the circumferential surface of the wire prior to winding the wire into a guidewire and a second tape-wrapping applied to the outer surface of the guidewire after winding the wire into a guidewire, it is possible to produce a guidewire with good handling properties by heat treating this guidewire only once, after the second tape-wrapping is applied.

Because the heat-treating process bonds the tape edges to the adjacent underlying or overlying tape surface, the tape-wrapped outer covering of the guidewire can be water-tight, and therefore is capable of preventing the passage of water and similar fluids between the exterior and interior surfaces of the guidewire. This characteristic helps prevent contamination of the guidewire by biological materials exterior to the guidewire surface. It also means that the interior of the guidewire may be used in the fashion of a catheter to convey fluids from one end of the guidewire to the other, that is, with adequate interior cross sectional area the guidewire of the present invention may be used as a catheter.

Heat-treated porous PTFE tape-wrapped coverings can also be water-tight. The hydrophobic characteristic of PTFE, combined with a small enough maximum pore size can prevent the passage of many types of fluids (for example, water) through the porous PTFE tape-wrapped outer surface covering. Porous PTFE has the further advantage of being gas permeable and may therefore allow the guidewire of the present invention to be used for the injection or withdrawal of gases.

Heat treating times and temperatures may be determined experimentally by those skilled in the art of processing fluoropolymers.

It is possible to increase the maximum pore size of porous PTFE with the application of additional heat. Heat can be applied to the distal end of a guidewire for a longer time or at a greater temperature than required by the previous heat-treating process in order to locally increase the permeability of the porous PTFE tape-wrapped covering to the point that it will allow the passage of liquids. If the spacing between adjacent windings of the guidewire distal end is increased so that they are not in contact, the guidewire can be used as a catheter for the injection or extraction of fluids through the permeable distal end covering. This technique can also be used to provide a valve at the distal end for turning off the flow of liquids as taught by U.S. Pat. No. 3,841,308.

An additional advantage of tape-wrapped coverings of porous PTFE is that the void spaces within the structure of the tape can be impregnated with other materials in order to carry those other materials into body cavities with the guidewire. These other materials are herein considered generically as chemicals and may include coagulant or anticoagulant agents, contrast medium, antibiotic or antimicrobial agents, various time-release drugs and lubricants.

Tape-wrapped fluoropolymer coverings can also be applied to other comparable catheter guidewire devices. For example, biopsy sample retrieval cables are made similarly to catheter guidewires. These devices are also comprised of a wire wound into a coil, generally of slightly larger outside coil diameter than the coiled wire of catheter guidewires. In addition, they incorporate one or more axially oriented control wires within the lumen of the coiled wire, the control wires intended to activate a cutting mechanism at the distal end of the device that is used to retrieve a tissue sample from a desired location within a living body. The flexibility and maneuverability requirements of biopsy sample retrieval cables are similar to those for catheter guidewires; therefore they also can benefit from the application of tape-wrapped fluoropolymer coatings.

Figure 9:
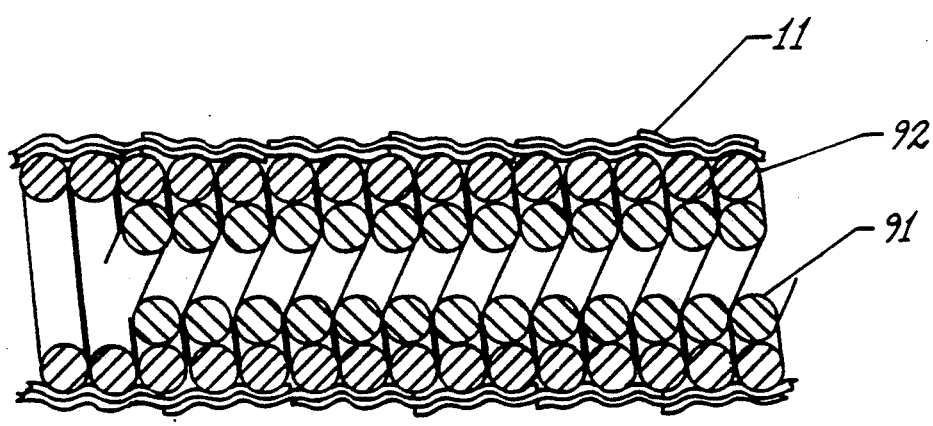
FIG. 9 shows a longitudinal section of an ultrasound drive shaft having a fluoropolymer tape-wrapped covering.

As shown by FIG. 9, ultrasound driveshafts (also known as ultrasound torque shafts) are likewise devices of the same type of construction as catheter guidewires, that is they are typically made of small gauge wire, usually of stainless steel, that has been wound into the form of a coil. Most typically, they are comprised of a first helically wound coil of wire 91 that is concentrically surrounded by a second helically wound coil of wire 92. The two coils are typically wound in opposite directions (that is, one was wound in a clockwise direction while the other was wound counter-clockwise). Therefore, when a rotary force is applied to such an ultrasound driveshaft in either a clockwise or counter-clockwise direction, the driveshaft is not subject to uncoiling. These driveshafts may be tape-wrapped with lubricious fluoropolymer tapes 11 in the same manner as catheter guidewires. The benefits of tape-wrapped ultrasound driveshaft coverings include having a thin, lubricious surface that allows smoother rotation and therefore more constant angular velocity of the driveshaft in order to provide a stable ultrasound image.

EXAMPLE 1

A catheter guidewire of 0.003 inch diameter stainless steel wire and having an outside diameter of 0.014 inches of the wound coil was tape-wrapped with an outer surface covering of porous PTFE tape, applied by the following process. First, a tape was cut from a roll of microporous expanded PTFE film manufactured according to the teachings of U.S. Pat. No. 3,962,153. This tape was about 0.0005 inch thick, 0.125 inch wide, and of less than about 1.0 g/cc density. A length of this tape was wound onto a small spool. Next, a cylindrical Delrin die was constructed as shown by FIG. 8, having a bored hole of 0.025 inch diameter wide access slot into the bored hole. The access slot was provided by cutting a ninety degree angular section from the cylindrical die, so that the corner of the section formed the slot. The spool of film was set up adjacent to the cylindrical die to enable the spool to pay tape through the access slot of the die as shown by FIG. 8. The distal end of the guidewire was inserted into the through-hole of the die and allowed to protrude from the other end of the hole. The end of the porous PTFE tape was pulled from the spool and wound several times around the distal end of the guidewire. The distal end of the guidewire was then pulled back into the bore of the through-hole (toward the proximal end) so that the tape fed through the access slot as shown by FIG. 8. The proximal end of the guidewire was gripped in a traversing chuck mechanism and rotated at about 330 RPM while being fed axially through the through-hole of the die by the traverse mechanism at a rate of about 2 per minute. A drag mechanism was used to resist rotation of the tape spool, thereby applying about 2 ounces of tension to the tape as it paid off of the tape spool and onto the surface of the rotating guidewire. The payoff angle, that is, the angle between the longitudinal axis of the guidewire and the centerline of the tape as it pays from the spool to the guidewire, was set so that the tape would feed from the spool without wrinkling onto the outer surface of the rotating and traversing guidewire. The tape-wrapped guidewire was then heat treated in an oven set at 380° C. for about 60 seconds in order to thermally bond adjacent tape layers together. After heat treating, the ends of the film were trimmed off even with the ends of the guidewire using a razor blade. The tape-wrapped guidewire appeared to be only slightly less flexible than the same guidewire before tape-wrapping. The tape-wrapped covering showed no indication of flaking after repeated bending of the guidewire.

Tension was applied to a short length of this tape-wrapped guidewire to determine the amount of force necessary to cause the wire to uncoil. This was done by placing the ends of this length into the grips of an Instron tester with a grip separation of 1.2 inches and crosshead speed of 2 inches per minute. A force of 0.6 pounds was required to cause extension and failure of the tape-wrapped covering and subsequent uncoiling of the tape-wrapped guidewire. The same test was applied to another sample of the same type of guidewire that had not been tape-wrapped; a force of less than 0.1 pounds was required to cause uncoiling.

EXAMPLE 2

A second guidewire of the same type as used in Example 1 was tape-wrapped and tested with the method and equipment described in Example 1. A non-porous tape of FEP (from Norton Performance Plastics, Wayne, N.J.) was used to wrap the outer surface of this guidewire. The guidewire was rotated at about 100 rpm while being fed axially along its longitudinal axis at 2 feet per minute. A tension of about 2 ounces was applied to the tape during wrapping. The wrapped guidewire was then heat treated in an oven set at 380° C. for a period of twenty seconds. After heat treating and cooling, the FEP tape-wrapped guidewire was subjectively examined for flexibility and possible flaking of the coating. This sample was not as flexible as the porous PTFE tape-wrapped guidewire of Example 1, however, it was felt to still have good flexibility and was deemed suitable for practical use. This sample also showed no evidence of flaking of the coating after repeated flexing. When tested for the amount of force required to cause uncoiling of the wire, it was found that 0.3 pounds was necessary.

EXAMPLE 3

Figure 10:
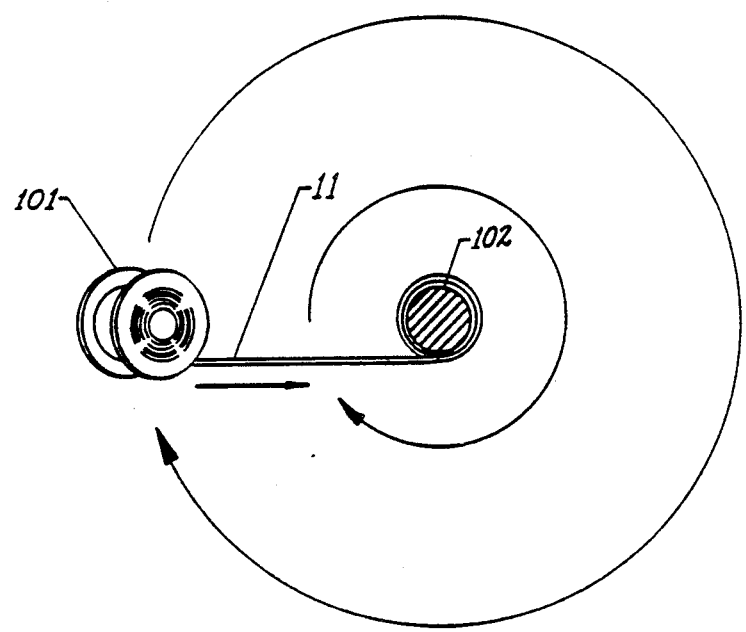
FIG. 10 shows the tape-wrapping method used to manufacture the catheter guidewire of Example 3 having a tape-wrapped covering applied to the wire before winding the wire into the coiled form of the guidewire.

A stainless steel wire of 0.002" diameter was wrapped with the same porous expanded PTFE tape as used in Example 1. The wire was wrapped using standard tape-wrapping equipment for insulating small gauge electrical wires. As shown by FIG. 10, a spool 101 of this tape 11 was rotated around the wire 102 at 600 rpm while the wire was fed at a rate of 0.492 inches per minute along its axis (around which the spool of tape was being rotated). The spool was able to rotate about its own axis, although drag was applied to this rotation to provide tension to the tape as it paid off of the spool on its way to wrap around the wire. The tape-wrapped guidewire was then heat treated for 15 seconds in an oven set at 380° C. and subsequently coiled into the form of a guidewire of 0.014 inch outside diameter. For comparison, an uncovered 0.002 stainless wire was also coiled into the form of a guidewire of the same dimensions. Bending and flexing of both samples revealed no apparent differences in the bending and handling characteristics of the two guidewires. Repeated bending of the tape-wrapped guidewire produced no evidence of flaking of the tape-wrapped covering.

Both samples were subsequently pulled in tension and rotated in order to simulate in vivo stresses. These forces were increased until uncoiling of the guidewires occurred. In both samples, the further application of traction and rotational forces caused looping and tangling of the uncoiled portion of the wire. Further tractional force caused the tangled wire to form a sharp kink which was followed by sudden breakage of the uncoated wire at the site of the kink. Conversely, the wrapped wire with the lubricious surface also tangled after uncoiling but no kinks were produced. It appeared that kinking did not occur because the lubricious tape-wrapped wire surface prevented the tangled wire from binding and gripping itself to produce a kink that would result in breakage. Instead, the tangled, tape-wrapped wire simply untangled and straightened out on the application of additional tension. Because kinking was avoided, the tensile strength of the wire was not compromised and the wire was not so easily broken.

EXAMPLE 4

An additional guidewire of the same type as describe 3 was produced from the same materials and by the same method except that the heat treating step was not performed after the tape-wrapped wire was wound into the form of a guidewire. An additional outer tape-wrapped covering was then applied with the same tape and method described in Example 1. After application of the second tape-wrapped covering, the guidewire was heat treated for 60 seconds in an oven set at 380° C. After removal from the oven and cooling to room temperature, this guidewire was subjected to repeated bending and flexing in order to compare its handling with another comparative guidewire made from the same wire wound to the same dimensions but not having any tape-wrapped coverings. It was found that the comparative guidewire was slightly more flexible but the tape-wrapped guidewire still exhibited good flexibility and was therefore deemed suitable for functional use as a catheter guidewire.

We claim:

1. A catheter guidewire device comprising a first length of helically wound wire having a covering of a fluoropolymer tape, said catheter guidewire device having distal and proximal ends, wherein the first length of helically wound wire has adjacent windings which are in direct contact so long as tension is not applied to the catheter guidewire device between the distal and proximal ends.

2. A catheter guidewire device according to claim 1 wherein the fluoropolymer tape is fluorinated ethylene propylene.

3. A catheter guidewire device according to claim 1 wherein the fluoropolymer tape is polytetrafluoroethylene.

4. A catheter guidewire device according to claim 3 wherein the fluoropolymer tape is porous polytetrafluoroethylene.

5. A catheter guidewire device according to claim 4 wherein the porous polytetrafluoroethylene tape is impregnated with a chemical.

6. A catheter guidewire device according to claim 1 wherein the guidewire has an outer surface and the fluoropolymer tape is helically wrapped around the guidewire outer surface.

7. A catheter guidewire device according to claim 1 wherein the catheter guidewire device has a longitudinal axis and an outer surface and the fluoropolymer tape is longitudinally wrapped around the catheter guidewire device outer surface, the tape having a longitudinal seam line parallel to the longitudinal axis of the catheter guidewire device.

8. A catheter guidewire device according to claim 1 wherein the first length of helically wound wire has a circumferential surface and the first length of helically wound wire circumferential surface has the covering of the fluoropolymer tape.

9. A catheter guidewire device according to claim 8 wherein the guidewire has an outer surface and has an additional fluoropolymer covering applied around the guidewire outer surface.

10. A catheter guidewire device according to claim 1 wherein the catheter guidewire device is a biopsy sample retrieval cable having a distal end and having a lumen within the first length of helically wound wire and further having at least one control wire within the lumen, the control wire attached to a cutting mechanism located at the distal end of the biopsy sample retrieval cable, said control wire enabling actuation of the cutting mechanism.

11. A catheter guidewire device according to claim 1 wherein the catheter guidewire device is an ultrasound driveshaft having a second length of helically wound wire within the first length of helically wound wire, the second length of helically wound wire being wound in a reverse direction to the first length of helically wound wire.

12. A catheter guidewire device according to claim 1 wherein said covering is water-tight.

13. A catheter guidewire device comprising a length of helically wound wire and an axially oriented safety wire within the helically wound wire, said safety wire having a covering of fluoropolymer tape.

* * * * *